United States Patent
Riser

(10) Patent No.: US 7,780,949 B2
(45) Date of Patent: Aug. 24, 2010

(54) REGULATION OF CCN2 BY CCN3 AND ITS THERAPEUTIC AND DIAGNOSTIC POTENTIAL IN FIBROSIS, SCLEROSIS AND OTHER DISEASES

(75) Inventor: Bruce L. Riser, Kenosha, WI (US)

(73) Assignee: Rosalind Franklin University of Medicine and Science, North Chicago, IL (US)

( * ) Notice: Subject to any disclaimer, the term of this patent is extended or adjusted under 35 U.S.C. 154(b) by 277 days.

(21) Appl. No.: 11/329,453

(22) Filed: Jan. 10, 2006

(65) Prior Publication Data
US 2006/0178332 A1 Aug. 10, 2006

Related U.S. Application Data

(60) Provisional application No. 60/646,916, filed on Jan. 25, 2005, provisional application No. 60/642,728, filed on Jan. 10, 2005.

(51) Int. Cl.
A61K 49/00 (2006.01)
A61K 49/14 (2006.01)
G01N 33/53 (2006.01)
G01N 33/50 (2006.01)

(52) U.S. Cl. .............................. 424/9.1; 514/2; 435/7.1; 702/19

(58) Field of Classification Search .................. None
See application file for complete search history.

(56) References Cited

U.S. PATENT DOCUMENTS

| 2003/0059768 A1* | 3/2003 | Vernet et al. .................. 435/6 |
| 2004/0009940 A1 | 1/2004 | Coleman et al. |
| 2004/0191230 A1 | 9/2004 | Auclair et al. |
| 2004/0224360 A1 | 11/2004 | Riser et al. |

FOREIGN PATENT DOCUMENTS

| EP | 1 382 347 A | 1/2004 |
| WO | WO2004/090109 A2 | 10/2004 |
| WO | WO 2006-036962 | 4/2006 |

OTHER PUBLICATIONS

Brigstock (2003). J. Endocrinology. 178, 169-175.*
Jeager et al. (2002) Am. J. Neurorad. 23, 200-207.*
Perbal. (2003) Exert Rev Molec Diag.3, 597-604.*
Perbal B., J Cell Commun Signal, 2(1-2):3-7, Jun. 2008.*
Yeger et al., J Cell Commun Signal, 1(3-4):159-164, Dec. 2007.*
Perbal B., NOV and the CCN family of genes: structural and functional issues. *J Clin. Pathol: Molecular Pathology* 54: 57-79, 2001.
Brigstock D. R., Regulation of angiogenesis and endothelial cell function by connective tissue growth factor and cystiene-rich 61 (CYR61). *Angiogensis* 5: 153-165, 2002.
Bradham MD et al, Connective tissue growth factor: a cysteine-rich mitogen secreted by human vascular endothelial cells is related to SCR-induced immediate early gene product CEF-10. *Journal of Cell Biology*, 114:1285-1294, 1991.
Tsai et al., Expression and function of CYR61, an angiogenic factor, in breast cancer cell lines and tumor biopsies. *Cancer Research* 60: 5603-5607, 2000.
Tsai et al., Expression and regulation of Cyr61 in human breast cancer cell lines. *Oncogene* 21: 964-973, 2002.
Sampath et al. Cyr61, a member of the CCN family, is required for MCF-7 cell proliferation: regulation by 17 beta-estradiol and overexpression in human breast cancer. *Endocrinology* 142: 2540-2548, 2001.
Sampath et al., Aberrant expression of Cyr 61, a member of the CCN family (i.e. CCN1), and dysregulation by 17 beta-estradiol and basic fibroblast growth factor in human uterine leiomyomas. *Journal of Clinical Endocrinology and Metabolism*, 86: 1707-1715, 2001.
Sampath et al, The angiogenic factor Cyr61 is induced by progestin R5020 and is necessary for mammary adenocarcinorma cell growth. *Endocrine*, 18: 147-159, 2002.
Xie et al., Breast cancer, Cyr61 is overexpressed, estrogen-inducible, and associated with more advanced disease. *Journal of Biological Chemistry*, 276: 14187-14194, 2001.
Xie et al., Elevated levels of connective tissue growth factor, WISP-1, and CYR61 in primary breast cancers associated with more advanced features. *Cancer Research*, 61: 8917-8923, 2001.

(Continued)

*Primary Examiner*—Stacey MacFarlane
(74) *Attorney, Agent, or Firm*—Rockey, Depke & Lyons, LLC; Joseph A. Fuchs

(57) ABSTRACT

The present invention discloses a role of CCN3 in diseases associated with the overexpression of CCN2, which include but are not limited to kidney disease, fibrosis, and cancer. The full length CCN3 protein or fragments thereof or isoforms (or combinations) of CCN3 are involved in these diseases. The isolated and purified CCN3 protein or its fragments or isoforms (or combinations) of CCN3 can be potentially used in the treatment or prevention of these diseases by regulating the expression and/or activity of the CCN2 protein. The level of CCN3 in tissue or body fluids can also be used to predict, diagnose and/or follow the progression of diseases as well as to determine the effectiveness of therapeutic intervention.

10 Claims, 9 Drawing Sheets

OTHER PUBLICATIONS

Rageh et al., Steroidal regulation of connective tissue growth factor (CCN2; CTGF) synthesis in the mouse uterus. *J. Clin. Pathol: Molecular Pathology*, 54: 338-346, 2001.

Cheon et al., A genomic approach to identify novel progesterone receptor regulated pathways in the uterus during implantation. *Molecular Endocrinology*, 16: 2853-2871, 2002.

Wandji et al., Messenger ribonucleic acids for MAC25 and connective tissue growth factor (CTGF) are inversely regulated during folliculogenesis and early luteogenesis. *Endocrinology*, 141: 2648-2657, 2000.

Slee et al., Differentiation-dependent expression of connective tissue growth factor and lysyl oxidase messenger ribonucleic acids in rat granulose cells. *Endocrinology*, 142: 1082-1089, 2001.

Harlow & Hillier, Connective tissue growth factor in the ovarian paracrine system. *Molecular and Cellular Endocrinology*, 187: 23-27, 2002.

Harlow et al., FSH and TGF-beta superfamily members regulate granulose cell connective tissue growth factor gene expression in vitro and in vivo. *Endocrinology*, 143: 3316-3325, 2002.

Liu et al., Gonodotrophins inhibit the expression of insulin-like growth binding protein-related protein-2 mRNA in cultured human granulose-luteal cells. *Molecular Human Reproduction*, 8:136-141; 2002.

Kyurkchiev S. et al., Potential cellular conformations of the CCN3 (NOV) protein. *Cellular Communication and Signaling*, 2: 9-18, 2004.

Li, C. L. et al., A role for CCN3 (NOV) in calcium signaling. *Journal of Clinical Pathology: Molecular Pathology*, 55: 250-261, 2002.

Dean R.G., Balding L., Candido R., Burns W.C., Cao Z., Twigg S.M., Burrell L,M. Connective tissue growth factor and cardiac fibrosis after myocardial infarction. *Journal of Histochemistry & Cytochemistry*. 53(10):1245-56, 2005.

Shi-wen X., Pennington D., Holmes A., Leask A., Bradham D., Beauchamp J.R., Fonseca C., du Bois R.M, Martin G.R., Black C.M., Abraham D.J. Autocrine overexpression of CTGF maintains fibrosis: RDA analysis of fibrosis genes in systemic sclerosis. *Experimental Cell Research*. 259(1):213-24, 2000.

Ozaki S., Sato Y., Yasoshima M., Harada K., Nakanuma Y. Diffuse expression of heparan sulfate proteoglycan and connective tissue growth factor in fibrous septa with many mast cells relate to unresolving hepatic fibrosis of congenital hepatic fibrosis. *Liver International*. 25(4):817-28, 2005.

Sakamoto N., Sugimura K., Kawashima H., Tsuchida K., Takemoto Y., Naganuma T., Tatsumi S., Nakatani T. Influence of glucose and inflammatory cytokines on TGF-beta1 and CTGF mRNA expressions in human peritoneal mesothelial cells. *International Journal of Molecular Medicine*. 15(6):907-11, 2005.

Zarrinkalam K.H., Stanley J.M., Gray J., Oliver N., Faull R.J. Connective tissue growth factor and its regulation in the peritoneal cavity of peritoneal dialysis patients. *Kidney International*. 64(1):331-8, 2003.

Riser, B. L. et al., Urinary CCN2 (CTGF) as a possible predictor of diabetic nephropathy: Preliminary report. *Kidney International*. 64: 451-458, 2003.

Wang S. Denichilo M. Brubaker C. Hirschberg R. Connective tissue growth factor in tubulointerstitial injury of diabetic nephropathy. *Kidney International*. 60(1):96-105, 2001.

Bernard Perbal: "The CCN3 (NOV) cell growth regulator: a new tool for molecular medicine" Expert Review of Molecular Diagnostics, Future Drugs, London, GB, vol. 3, No. 5, Sep. 1, 2003, pp. 597-604, XP009100681 ISSN: 1473-7159.

Brigstock D R: "The CCN family: a new stimulus package" Journal of Endocrinology, Bristol, GB, vol. 178, No. 2, Aug. 1, 2003, pp. 169-175, XP002323770 ISSN: 0022-0795.

* cited by examiner db/db: diabetic kidney db/m: nondiabetic kidney db/db: diabetic kidney db/m: non-diabetic kidney

REGULATION OF CCN2 BY CCN3 AND ITS THERAPEUTIC AND DIAGNOSTIC POTENTIAL IN FIBROSIS, SCLEROSIS AND OTHER DISEASES

CROSS-REFERENCE TO RELATED APPLICATION

This application claims priority from provisional applications Ser. No. 60/642,728 filed Jan. 10, 2005, and Ser. No. 60/646,916 filed Jan. 25, 2005, which are both incorporated herein by reference and made a part hereof.

FEDERALLY SPONSORED RESEARCH OR DEVELOPMENT

Not Applicable.

BACKGROUND OF THE INVENTION

Field of the Invention

The present invention discloses a role of CCN3 in diseases associated with the overexpression of CCN2, which include but are not limited to kidney disease, fibrosis, and cancer. The CCN3 can be a full length CCN3 protein or a fragment thereof, or an isoform of the full length CCN3, or a combination thereof. The isolated and purified CCN3 can be potentially used in the treatment of these diseases by regulating the expression and/or activity of the CCN2 protein. The level of CCN3 in tissue or body fluids can also be used to predict, diagnose and/or follow the progression of diseases as well as to determine the effectiveness of therapeutic-intervention.

The CCN Family of Genes and Proteins

The CCN family of genes presently consists of six distinct members encoding proteins that participate in fundamental biological processes such as cell proliferation, attachment, migration, differentiation, wound healing, angiogenesis, and several pathologies including fibrosis and tumorigensis. Proteins encoded by the members of the CCN gene family are 30-40 kDa proteins extremely rich in cysteine (10% by mass) (Perbal B., NOV and the CCN family of genes: structural and functional issues. *Molecular Pathology* 54: 57-79, 2001). More recently, it has been reported that some forms of the CCN proteins (CCN3 included) are in the 35-55 kDa range. They are designated as cysteine-rich 61 (CYR-61) proteins, connective tissue growth factor (CTGF) proteins, nephroblastoma overexpressed (NOV) proteins, Wnt-induced secreted proteins-1 (WISP-1), Wnt-induced secreted proteins-2 (WISP-2), and Wnt-induced secreted proteins-3 (WISP-3). More recently, new nomenclature for this family of genes and proteins has been proposed (see Table 1).

TABLE 1

Proposed Names and Names Currently and Previously Used for CCN Family of Genes and Proteins

| Proposed name | Names used currently or previously |
|---|---|
| CCN1 | CYR61 (human, mouse, *xenopus*), CEF10 (chicken), IGFBP-rP4 (human), βIG-M1 (mouse), CTGF-2, IGFBP10 (human), angiopro |
| CCN2 | CTGF (human, mouse, chicken, *xenopus*), βIG-M2 (mouse), FISP12 (mouse), IGFBP-rP2 (human), Hsc24 (human), IGFBP8 (human), HBGF-0.8, ecogenin (human) |
| CCN3 | NOV (human, rat, chicken, mouse, quail), IGFBP-rP3 |

TABLE 1-continued

Proposed Names and Names Currently and Previously Used for CCN Family of Genes and Proteins

| Proposed name | Names used currently or previously |
|---|---|
| | (human), IGFBP9 (human), NOVH (human), NOVm, mNOV (mouse), xNOV (*xenopus*) |
| CCN4 | WISP-1 (human), ELM-1 |
| CCN5 | WISP-2 (human), CTGF-L, CTGF-3, HICP, rCOP-1 (rat) |
| CCN6 | WISP-3 (human) |

FIG. 1 shows the modular structure of the CCN proteins. Although they have a very conserved multimodular organization, with four modules sharing identity with insulin-like growth factor binding proteins (IGFBPs), Von Willebrand factor (VWC), thrombospondin-1 (TSP1), and a cysteine knot (CT) containing family of growth regulators, the CCN proteins have distinctive biological properties and are differentially regulated. Their involvement has been shown in multiple organ systems. One organ that has been the focus of a large number of studies is the kidney. The underlying mechanisms of action of CCN proteins are still poorly understood. Attempts to identify unique specific high-affinity signal transducing receptors have been fruitless. (Brigstock D. R., Regulation of angiogenesis and endothelial cell function by connective tissue growth factor. *FEBS Letters* 327: 125-130, 2003).

CCN2 Gene and Its Encoded Protein

Of all the six members of the CCN family, CCN2 has emerged as an important player in its roles in the regulation of certain cellular functions important in skeletal growth and placental angiogenesis, as well as its roles in certain diseases including fibrosis (renal and diabetes associated fibrosis) and perhaps tumorigenesis.

Studies with the renal system have provided evidence of the role of CCN2 as an important pathogenic factor in fibrosis/sclerosis in a number of models of chronic kidney disease (CKD). Early reports suggested a possible interactive role with transforming growth factor-beta (TGF-β) in skin fibrosis and scleroderma (Bradham D M et al, Connective tissue growth factor: a cysteine-rich mitogen secreted by human vascular endothelial cells is related to SCR-induced immediate early gene product CEF-10. *Journal of Cell Biology*, 114: 1285-1294, 1991).

The formation of sclerosis or fibrosis in the kidney is a common response to severe or chronic forms of injury. At least in chronic kidney disease (CKD), there appears to be three predominant causal factors: metabolic, genetic, and hemodynamic. All of these factors can interact, particularly in diabetic nephropathy (DN), to drive progression. CCN2 now appears to be a central, downstream mediator of the effects of these three elements. For example, pathological shear or stretching force resulting from intraglomerular hypertension appears to stimulate the production of cytokines including CCN2. This same force appears to be responsible for increased vascular permeability leading to both proteinuria and an increased production of vasoactive hormones such as angiotensin (AG) II and endothelin, which in turn also elevate CCN2 and further enhance the mechanical force. The abnormal accumulation of advanced glycosylation end products (AGEs) that occur with the altered metabolism of glucose in DN may also work to both directly increase extracellular matrix (ECM) cross-linking and accumulation, as well as to increase CCN2. The genetic background of the individual can influence the elements of hemodynamics and metabolism, and in turn the resulting pathways as described. Additionally there is a likely influence of genetics on protein kinase C (PKC) activity and production of vasoactive hormones. In all cases, the chronic upregulation of CCN2 activity is likely to result in altered ECM turnover and increasing ECM accumulation, producing fibrosis or sclerosis. These findings support the postulate that CCN2 is a central downstream element in the progression of renal fibrosis, and as such provides a reasonable and novel target for both diagnostics and therapeutic purposes.

CCN2 is estrogen inducible and overexpressed in steroid-dependent breast or uterine tumors (Tsai et al., Expression and function of CYR61, an angiogenic factor, in breast cancer cell lines and tumor biopsies. *Cancer Research* 60: 5602-5607, 2000; Tsai et al., Expression and regulation of Cyr61 in human breast cancer cell lines. *Oncogene* 21: 964-974, 2000; Sampath et al. Cyr61, a member of the CCN family, is required for MCF-7 cell proliferation: regulation by 17 beta-estradiol and overexpression in human breast cancer. *Endocrinology* 142: 2540-2548, 2001; Sampath et al., Aberrant expression of Cyr 61, a member of the CCN family (i.e. CCN1), and dysregulation by 17 beta-estradiol and basic fibroblast growth factor in human uterine leiomyomas. *Journal of Clinical Endocrinology and Metabolism*, 86: 1707-1715, 2001; Sampath et al, The angiogenic factor Cyr61 is induced by progestin R5020 and is necessary for mammary adenocarcinorma cell growth. *Endocrine*, 18: 147-150, 2002; Xie et al., Breast cancer, Cyr61 is overexpressed, estrogen-inducible, and associated with more advanced disease. *Journal of Biological Chemistry*, 276: 14187-14194, 2001; Xie et al., Elevated levels of connective tissue growth factor, WISP-1, and CYR61 in primary breast cancers associated with more advanced features. *Cancer Research*, 61: 8917-8923, 2002). CCN2 and other CCN family members are important downstream mediators of estrogen- and progesterone-regulated cell growth. CCN2 and other CCN proteins may also impact other growth regulatory pathways in breast cancer cells. Uterine CCN2 is regulated by both estrogen and progesterone and appears to be important for maintenance or remodeling of stromal ECM (Rageh et al., Steroidal regulation of connective tissue growth factor (CCN2; CTGF) synthesis in the mouse uterus. *Molecular Pathology*, 56: 80-85, 2001; Cheon et al., A genomic approach to identify novel progesterone receptor regulated pathways in the uterus during implantation. *Molecular Endocrinology*, 16: 2853-2871, 2002). In the ovary, CCN2 is regulated by gonadotropins or transforming growth factor-beta (TGF-β) and is associated with thecal cell recruitment and mitosis, and maintenance of the corpus luteum (Wandji et al., Messenger ribonucleic acids for MAC25 and connective tissue growth factor (CTGF) are inversely regulated during folliculogenesis and early luteogenesis. *Kidney International*, 60: 96-105, 2000; Slee et al., Differentiation-dependent expression of connective tissue growth factor and lysyl oxidase messenger ribonucleic acids in rat granulose cells. *Endocrinology*, 142: 1082-1089, 2001; Harlow & Hillar, Connective tissue growth factor in the ovarian paracrine system. Molecular and Cellular Endocrinology, 187: 23-27, 2002; Harlow et al., FSH and TGF-beta superfamily members regulate granulose cell connective tissue growth factor gene expression in vitro and in vivo. *Endocrinology*, 143: 3316-3325, 2002; Liu et al., Gonadotrophins inhibit the expression of insulin-like growth binding protein-related protein-2 mRNA in cultured human granulose-luteal cells. *Molecular Human Reproduction*, 8: 136-141; 2002).

U.S. Patent Application Serial No. US20040224360 by Riser and DeNichilo discloses the role of CCN2 in the production of extracellular matrix (ECM), as well as methods for diagnosing the presence and progress of pathologies characterized by an accumulation of the ECM components by measuring the level of CCN2 in a sample. The method is directed to diagnosing kidney fibrosis and associated renal disorders, in particular, complications associated with diabetes, hyperglycemia, and hypertension.

CCN3 Gene and Its Encoded Proteins

CCN3 is another member of the CCN family. It has been reported that CCN3 exists in various forms. In a study to construct retroviral competent ovian recombinants, it has been demonstrated that the CCN3 protein can be expressed either as a full length protein with a molecular weight of about 50 kDa or a smaller truncated protein, which is a fragment of the full length protein (Perbal B., *J. Clin. Pathol: Mol Pathol*. 54: 57-79, 2001). Other forms of CCN3 protein have also been reported. For example, a CCN3 related protein has been detected at the nuclear envelope of the NCl-H295R cells and another CCN3 related protein binds the promoter of human plasminogen activator inhibitor type 2 (PAI-2) (Perbal B., *J. Clin. Pathol. Mol Pathol,* 54: 57-79, 2001). K19M-AF antibody directed against C-terminal 19-aminoacid peptide of CCN3 revealed at least two conformational states of the native CCN3 protein (Kyurkchiev S. et al., Potential cellular conformations of the CCN3 (NOV) protein. *Cellular Communication and Signaling,* 2: 9-18, 2004). Cytoplasmic and cell membrane bound CCN3 has an exposed C-terminus while secreted CCN3 has a sequestered C-terminus which could be due to interaction with other proteins or itself (dimerization).

The amino acid sequences of the full length CCN3 proteins from various species, including human, have been fully characterized and are disclosed by Li et al. (Li, C. L. et al., A role for CCN3 (NOV) in calcium signaling. *Journal of Clinical Pathology: Molecular Pathology,* 55: 250-261, 2002).

These and other aspects and attributes of the present invention will be discussed with reference to the following drawings and accompanying specification.

DETAILED DESCRIPTION OF THE INVENTION

Figure 1:
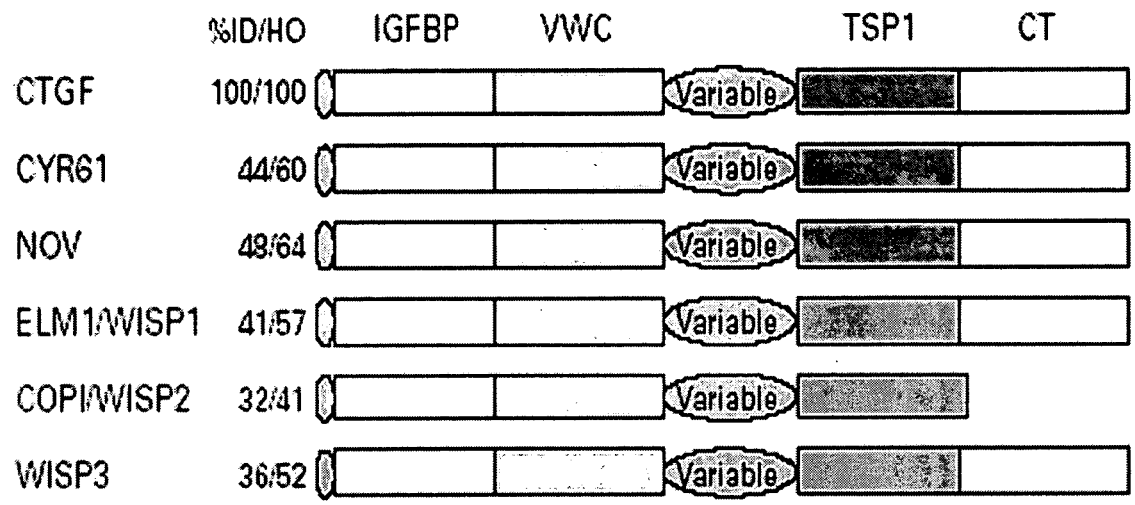
FIG. 1 shows the multimodular structure of the CCN proteins. CT, cysteine knot containing family of growth regulators-like domain; IGFBP, insulin-like growth factor binding protein-like domain; TSP1, thrombospondin-like domain; and VWC, Von Willebrand factor-like domain.

While this invention is susceptible of embodiment in many different forms, there is shown in the drawing, and will be described herein in detail, specific embodiments thereof with the understanding that the present disclosure is to be considered as an exemplification of the principles of the invention and is not intended to limit the invention to the specific embodiments illustrated.

The present invention discloses a role of CCN3 in diseases associated with the overexpression of CCN2, which include but are not limited to kidney disease, fibrosis, and cancer. The CCN3 can be a full length CCN3 protein with a molecular weight of about 50 kD or a fragment thereof, or an isoform of the full length CCN3, or a complex comprising one or more forms of CCN3, or a combination thereof. What is meant by the term "isoform" in the present disclosure is that each isoform is immunoreactive to one or more antibodies against the full length CCN3 molecule, but may not exactly resemble the full length form as previously reported, in terms of molecular weight, amino acid sequence, three dimensional configuration, of post translational modification(s). The isolated and purified CCN3 can be potentially used in the treatment of these diseases by regulating the expression and/or activity of the CCN2 protein. The level of CCN3 in tissue or body fluids can also be used to predict, diagnose and/or follow the progression of diseases as well as to determine the effectiveness of therapeutic intervention.

The term "fibrosis" used in the present disclosure is used interchangeably with the term "sclerosis" since they are similar processes involved in the overgrowth of fibrous or fibrosis-like tissue and/or the increased deposition of extracellular matrix molecules such as collagen, and both have been shown to have CCN2 as at least a causal factor. The term "fibrosis" in the present disclosure can also include fibrosis and/or sclerosis.

CCN2 has been now shown to be a causal factor in renal fibrosis, and appears to act in a similar fashion in other fibrotic diseases, including those occurring in the liver, lungs, heart, skin, vasculature, peritoneum, etc (Dean R. G., Balding L., Candido R., Burns W. C., Cao Z., Twigg S. M., Burrell L, M. Connective tissue growth factor and cardiac fibrosis after myocardial infarction. *Journal of Histochemistry & Cytochemistry.* 53(10):1245-56, 2005, Shi-wen X., Pennington D., Holmes A., Leask A., Bradham D., Beauchamp J. R., Fonseca C., du Bois R. M., Martin G. R., Black C. M., Abraham D. J. Autocrine overexpression of CTGF maintains fibrosis: RDA analysis of fibrosis genes in systemic sclerosis. *Experimental Cell Research.* 259(1):213-24, 2000; Ozaki S., Sato Y., Yasoshima p4., Harada K., Nakanuma Y. Diffuse expression of heparan sulfate proteoglycan and connective tissue growth factor in fibrous septa with many mast cells relate to unresolving hepatic fibrosis of congenital hepatic fibrosis. *Liver International.* 25(4):817-28, 2005; Sakamoto N., Sugimura K., Kawashima H., Tsuchida K., Takemoto Y., Naganuma T., Tatsumi S., Nakatani T. Influence of glucose and inflammatory cytokines on TGF-beta1 and CTGF mRNA expressions in human peritoneal mesothelial cells. *International Journal of Molecular Medicine.* 15(6):907-11, 2005, Zarrinkalam K. H., Stanley J. M., Gray J., Oliver N., Faull R. J. Connective tissue growth factor and its regulation in the peritoneal cavity of peritoneal dialysis patients. *Kidney International.* 64(1):331-8, 2003.). When expressed in increased amounts, CCN2 upregulated, for example, by transforming growth factor-β (TGF-β), high glucose concentrations, mechanical stress, advanced glycosylation end products (AGEs), induces (among other things) the over-accumulation of extracellular matrix (ECM) molecules (e.g., collagen forms and thrombospondin (TSP)), resulting in scarring and fibrosis/sclerosis. CCN3 has enough similarities in structure to be recognized as belonging to the CCN family of genes. CCN3, unlike CCN2, has not been reported to be involved in the regulation of collagen, thrombospondin or fibrosis, and in fact, most of the members of the CCN family have been reported to have, for the most part, different biological activities.

Excretion of CCN3 in Urines of Patients with Diabetes and with Renal Fibrosis

To show a role for CCN3 in fibrosis, and in particular renal fibrosis in diabetes disease, diabetic patients at different stages of renal disease were examined for their excretion of CCN3 in urine. Diabetic patients can also serve as a model for many other forms of both renal and extra-renal fibrosis/sclerosis, including chronic kidney disease (CKD). It has previously been shown that patients with CKD have increased amounts of CCN2 present in the kidney, and they also excrete CCN2 in urine. The level of CCN2 appears to be related to progression of the disease, with increased amounts correlating with increased progression of the disease (see U.S. Patent Application No. US2004-0224360 by Riser and DeNichilo). We show in the current application, for the first time, that healthy human subjects with no known history of renal diseases (referred hereafter as "healthy human subjects" or "healthy subjects") also excrete CCN3 in their urine. This was first determined in this study by ELISA, using a CCN3 specific antibody. The amount of CCN3 in healthy human subjects was approximately 280 (+/−377) μg/mmol creatinine. This is much higher, on average, than the levels of CCN2 in the healthy human subjects, which is approximately 2.0 (+/−2.0) μg/mmol creatinine. In diabetic patients without clinical renal disease (normoalbuminuric patients), the average levels of CCN3, at 350 (+/−574) μg/mmol creatinine, were similar to the CCN3 levels of the healthy control group. In patients in the earliest stage of renal disease (i.e. albuminuric patients), the CCN3 levels as a group were increased to the average level of 3,048 (+/−6,599) μg/mmol creatinine. Individually, seven of the 13 albuminuric patients in the group had levels of CCN3 elevated over what was found to be normal, for healthy persons. In patients with advanced clinical renal disease (i.e. proteinuric patients) the levels were further and greatly increased to 27,526 mean (+/−65,301) μg/mmol creatinine, or in terms of mg, 27.5 mg/mmol creatinine. In contrast, urinary CCN2 levels in healthy subjects and diabetic patients without kidney disease had comparably low levels (2.0 and 2.4 (+/−2.3 and 6.8) μg/mmol creatine) or approximately 100-fold less CCN2 than CCN3. Patients that develop renal disease followed a somewhat different course of expression that appeared, at the later stage, to be a response to CCN3. For example, the CCN2 expression was increased in a limited number of patients early, i.e. before albuminuria but the average remains like that of non-renal or healthy subjects (1.1+/−1.6 ng/mmol creatinine). In the proteinuric group the average rose to 18.7 ng/mmol creatinine, but then appear to fall with time back toward baseline, as the CCN3 values increase. This indicated that CCN3 is involved in the progression of disease, possibly as an endogenous inhibitor of CCN2 (a known causal factor in disease progression). This suggested that CCN3 may provide a negative regulatory element for CCN2, and that levels in urine may serve to predict, or stage, the patient's progression toward renal failure. These data also indicate that the CCN3 can be isolated and purified from urine of human subjects. Particularly, patients with various renal diseases in which CCN3 is overexpressed provide an excellent source of obtaining CCN3 in large quantities. It will be apparent from studies described below that CCN3 can be found in other body fluids or tissues of human subjects and other animal species which can also serve as excellent sources for the isolation and purification of the CCN3 protein.

Figure 2:
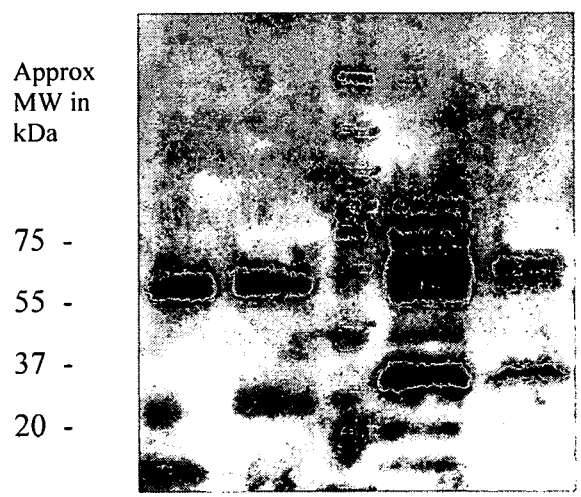
FIG. 2 is a Western (immunoblot) blot analysis for CCN3 reactive proteins, showing multiple bands in the urine of a patient with diabetic nephropathy with the sample being run both undiluted or diluted 1:10. A conditioned medium from a cell line (NCI) producing high amounts of CCN3 was run as a positive control (left 2 lanes). Approximate molecular weights in kDa (marked in lane M) are shown numerically on the left of the figure.

Immunoblotting analysis of urine samples confirmed the presence of CCN3 in urine and identified the presence of multiple molecular forms (isoforms) of CCN3 in patients with diabetic disease. Urine samples from healthy subjects demonstrated only a single band equivalent to the naturally produced full length CCN3 with a molecular weight of about 50 kDa Urine samples from diabetic patients demonstrated, in addition to the full length CCN3, forms of both lower and higher molecular weight immunoreactive CCN3 (FIG. 2, right lanes) suggesting that these alternative forms, which include fragments, isoforms, or combinations comprising one or more forms of the CCN3 molecule or its fragments or its isoforms, may be important in the progression of the disease. What is meant by the term "isoform" in the present disclosure is that each isoform is immunoreactive to one or more antibodies against the full length CCN3 molecule, but may not exactly resemble the full length form as previously reported, in terms of molecular weight, amino acid sequence, three dimensional configuration, of post translational modification(s).

CCN3 in Dialysis Fluids from Patients Undergoing Successful Peritoneal Dialysis

In order for patients with end stage renal disease (ESRD) to survive as the kidneys fail, they can choose from 3 available types of renal replacement therapy. This is also true of patients with a variety of other renal diseases, including acute renal failure. One replacement therapy is a renal transplant, but it is not acceptable or available to many patients. A second therapy type is hemodialysis, which requires long and physically demanding sessions (most commonly three times weekly) in a dialysis clinic. The third type of therapy is peritoneal dialysis, and most often can be done by the patient at home. Therefore, peritoneal dialysis is the best option for many. One of the greatest impediments to this as a successful long-term therapy is the tendency for many patients to develop, over time, fibrosis of the peritoneal membrane with the eventual loss of the ability to transport the dialysis fluid necessary for the removal of toxic byproducts of metabolism from the blood. There are no treatments available for this type of fibrosis, and currently there is no way to predict how long the patient will be able to use this type of dialysis.

We examined the peritoneal dialysis fluids (also known as dialysate samples) from patients undergoing successful dialysis (i.e., without the obvious development of fibrosis of the peritoneal membrane, as determined by inadequate ultafiltration across the membrane) for the presence of CCN3, and for comparison of CCN2 levels. In the 51 patients tested by ELISA, surprisingly, it was discovered that most of these patients had CCN3 levels in the dialysis fluids in the range of 6-28 ng/ml. In contrast, most of the patients tested did not have detectable levels of CCN2 (i.e., below 2 ng/ml). Only two out of 51 patients tested had elevated CCN2 levels (18.6 and 18.5 ng/ml, respectively). This suggests that CCN3, or a fragment or molecular isoform of CCN3 may play a role in the peritoneal fibrosis, but unlike CCN2, it, or a fragment or molecular isoform, may act as an inhibitor of fibrosis.

Figure 3:
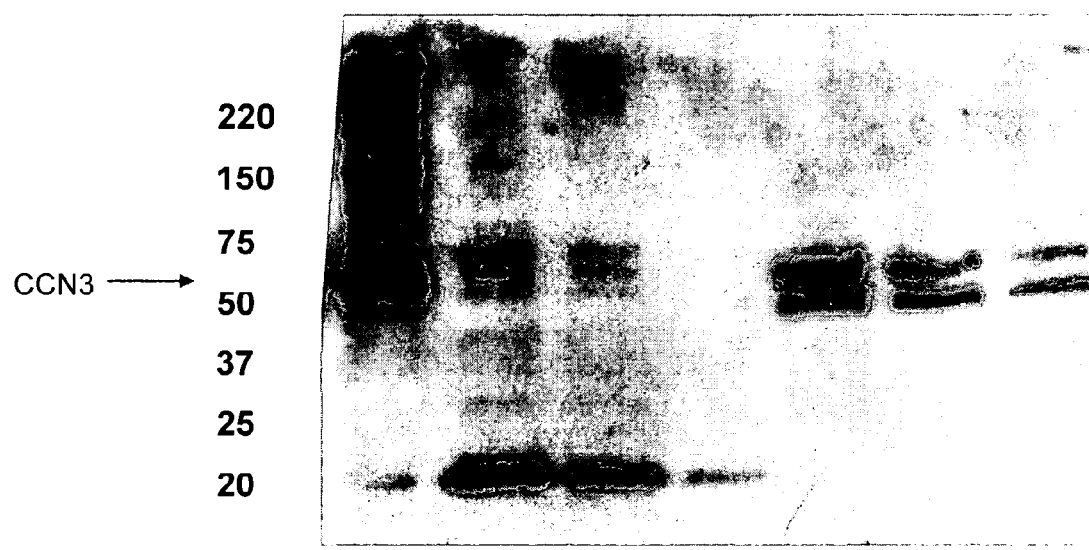
FIG. 3 is a Western (immunoblot) blot analysis of mouse urine and human peritoneal dialysate (PD) fluids using a CCN3 specific antibody. Human PD fluids demonstrated two definitive CCN3 bands at approximately 50 and 65-70 kDa, compared to a conditioned medium containing a high concentration of CCN3 (GST-NOV, far left lane). Mouse urine CCN3 appeared as 3 bands at approximately 50, 60, and 70 kDa, as well as a single more intense staining band at approximately 15-20 kDa. The latter 15-20 kDa band may represent a quarter fragment of the full length molecules.
Figure 4:
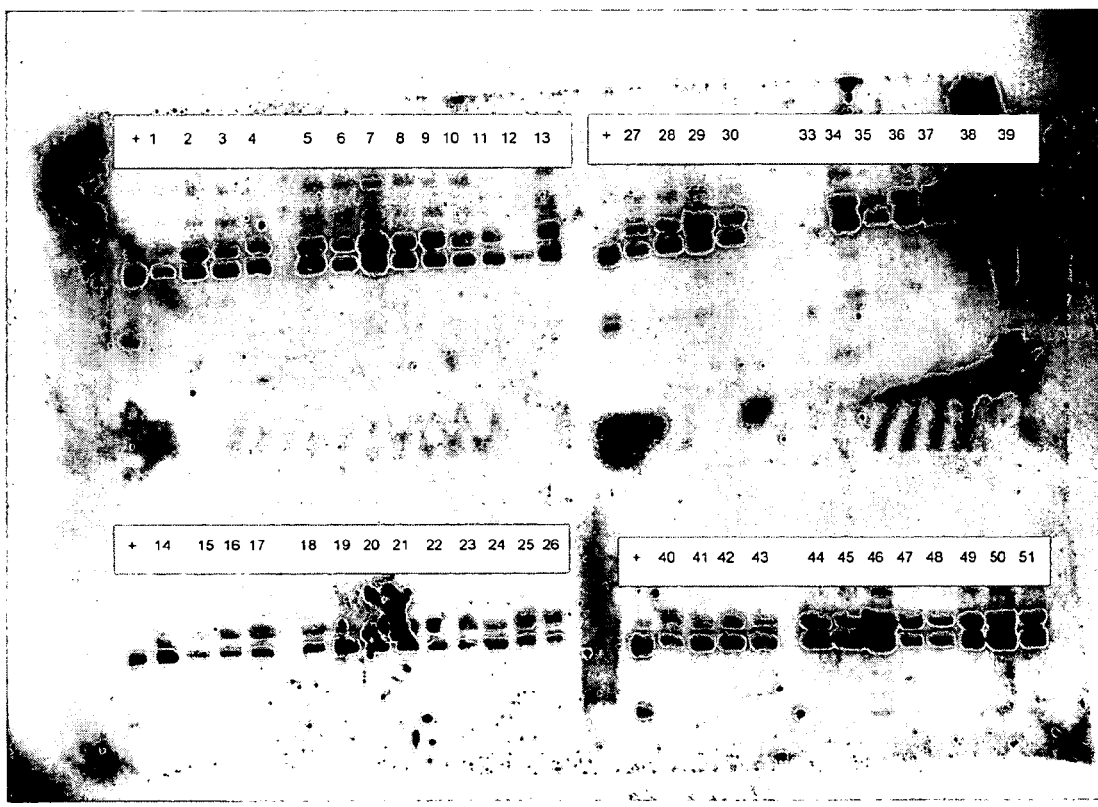
FIG. 4 is a Western or immunoblot (four gels run at the same time under the same conditions) of dialysis fluids collected from patients undergoing successful dialysis (i.e. without the obvious development of fibrosis of the peritoneal membrane, as determined by adequate ultrafiltration across the membrane) and demonstrated the presence of immunoreactive CCN3 molecules. Although most patients demonstrated two prominent bands at the 50-65 kDa range (determined by comparison to molecular weight standards on the orginal gel), some patients demonstrated little staining whereas others demonstrated intense staining, and a few samples showed the presence of alternative sizes including a band at approximately 20 kDa. The lane marked (+) contained culture medium enriched for CCN3 as a positive control, and demonstrated 2 intense bands with one strong band at approximately 50-55 kDa, and another strong band at approximately 20 kDa. The 20 kDa band is thought to represent a fragment of the CCN3 molecule cleaved at the center. A third lighter band appeared at 60-65 kDa, eqivalent in size to a strong band seen in most patient fluids.

Western blot analysis of human peritoneal dialysis (PD) fluids (also known as dialysate samples) from successful peritoneal dialysis (i.e., without developing fibrosis of the peritoneal membrane) using CCN3 specific antibody (see FIG. 3) demonstrated two definitive CCN3 bands at approximately 50 and 65-70 kDa when compared to a molecular weight standard. In contrast, urine CCN3 (in this case mouse) appeared as 3 bands at approximately 50, 60, and 70 kDa, as well as a single band at approximately 15 kDa. The latter 15 kDa band may represent a quarter fragment of the full length molecule. As shown in FIG. 4, when dialysate samples from patients receiving successful peritoneal dialysis were examined by Western blot analysis, most patients demonstrated two prominent bands at the 50-65 kDa range. However some patients demonstrated light staining for these bands whereas a few samples showed the presence of alternative sizes of CCN3 reactive molecule, including a band at approximately 20 kDa.

These results demonstrated for the first time the presence, not only of CCN3 in PD fluids of diabetic patients with successful peritoneal dialysis, but also of unique isoforms. This suggests, among other things, that patients with high levels of peritoneal CCN3 (or CCN3 fragments or isoforms or a combination thereof) may protect against fibrosis in that location, at least in part by controlling (or downregulating) CCN2 (and possibly other pro-fibrotic factors, including some other CCN family members). Patients with high initial CCN3 levels may be those most resistant to the development of peritoneal fibrosis and the loss of ultrafiltration capacity upon continued dialysis treatment, and therefore most suitable to long term PD therapy. This also provides evidence that CCN3 may be used to treat or protect diabetic patients from the development of fibrosis, and or the loss of untrafiltration capacity in dialysis (whether diabetic or not) particularly in those patients that have either low initial levels, or those that have levels reduced following peritoneal dialysis. As used in the present disclosure, CCN3 includes but is not limited to the full length CCN3 protein, a fragment thereof, an isoform of the full length CCN3 protein, a recombinant CCN3 protein, a molecular mimetic of CCN3, or a complex comprising one of the forms of CCN3, or any combination of one or more forms of CCN3. What is meant by "isoform" is the molecule is immunoreactive to one of more antibodies specific to the full length CCN3. They can be administered to a patient by any traditional routes suitable for delivering macromolecules, such as intravenous, intramuscular, nasal, topical, transdermal, inhalation, oral, and the like. These routes of administration are well known to those skilled in the art. One method for administration of a CCN3-based therapy for preventing or reversing peritoneal fibrosis in patients undergoing peritoneal dialysis would be the addition of the CCN3 to dialysis solutions to be used by the patients to undergo peritoneal dialysis.

Data from an Animal Model of Type 2 Diabetes and Renal Disease

The db/db mouse model of type 2 diabetes was also used to establish a role for CCN3 in renal and fibrotic diseases. The db/db mouse becomes quickly obese and develops hyperglycemia within approximately 1 month of age. Over the subsequent 3-4 months, the mice develop renal glomerular fibrosis characteristic of human renal disease. However, the disease, unlike that seen in humans, does not continue to progress to advanced glomerular sclerosis, and/or interstitial disease, let alone subsequent renal failure, but appears to remain in a "static-like disease state". The control, db/m littermates are identical to the db/db mice except they do not express the mutational phenotype, and do not become obese, develop diabetes, or kidney disease. As in the case in human patients, mice made diabetic were found by ELISA to contain CCN2 in urine (Riser, B. L. et al., Urinary CCN2 (CTGF) as a possible predictor of diabetic nephropathy: Preliminary report. *Kidney International.* 64: 451-458, 2003). In the present disclosure, the control, non-diabetic mice were discovered to have CCN3 levels in the urine of approximately 204 µg/mmol urinary creatinine. Urinary creatinine was measured and used as a way to standardize samples, since diabetic patients and animals urinate more frequently producing more diluted urine. In contrast to the control animals, those with diabetes increased their levels of urinary CCN3 6-fold, to 1,244 µg CCN3/mmol creatinine within 4 weeks of becoming diabetic. By two months of diabetes the values returned to 334 µg CCN3/mmol creatinine, and remained low at 3 months (31.2 µg CCN3/mmol creatinine) and 6 months (27.5 µg CCN3/mmol creatinine in diabetic animals, and 28.3 in non-diabetic control animals), the last period examined. In summary, in the db/db model of type 2 diabetes, CCN3 increased greatly within a month of diabetes, as measured in urine. Then, over time, the CCN3 levels decreased to that of the control, non-diseased animals. This supports the idea that CCN3 is involved in diabetes and renal disease. CCN3 in already high levels in the healthy animals (i.e. relative to CCN2) may act to keep constitutive levels of CCN2 low, as a negative regulator. CCN2 is then increased following the onset of diabetes as a response to injury (wound healing response), or a metabolic stress event, overcoming the downregulation of the CCN3 present. Because this metabolic stress is chronic, the signal for increased CCN2 remains present. The normal method for negative feedback of this signal would appear from this data to be CCN3. Therefore, the observed upregulation in CCN3 would be a response to the early, but somewhat long-term increase in CCN2, with CCN3 then being a negative regulator of CCN2 expression, controlling the expression and or activity of the latter. This overall repair mechanism would allow for a needed response of CCN2 to acute injury, but when chronic, would need to be shut down. If not shut down properly, the fibrosis would, and does, ensue.

Figure 5:
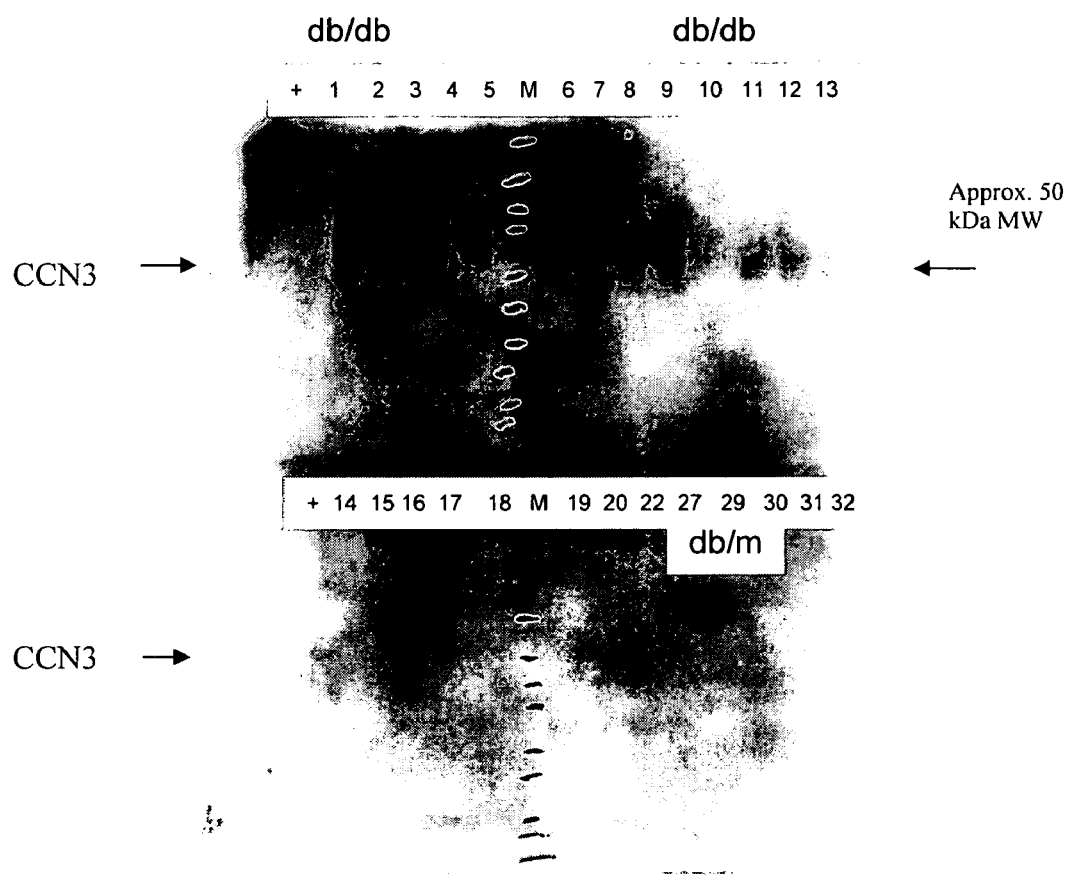
FIG. 5 is a Western blot analysis of urine samples from diabetic (db/db) (lanes 1-16) and non-diabetic (db/m) (lanes 17-32) mice demonstrating the presence of a faint CCN3 band in one non-diabetic animal (lane 20), and strong CCN3 band (s) in most diabetic animals with "static" renal disease. M=molecular weight standards.

Immunoblotting was used to determine the identity of the CCN3 molecular form present (i.e., a qualitative, rather than quantitative assay). Urine from db/m control mice showed only a single CCN3 band, and was present in one of 6 mice (FIG. 5). However, db/db mice demonstrated multiple CCN3 bands that were present in almost all of the diseased mice. This result supports the finding described above for the quantitative ELISA assay, but in addition demonstrates that in diseased animals, there are not only increased levels of CCN3, but multiple isoforms, fragments, or multicomplexes. Isolation and characterization of these unique forms from the urine (and/or PD fluids) could be used to determine molecules, or molecular forms that have unique, or maximal therapeutic potential, for use as extracted, and/or purified or produced in a recombinant form in a cell, tissue, or other system.

Figure 6:
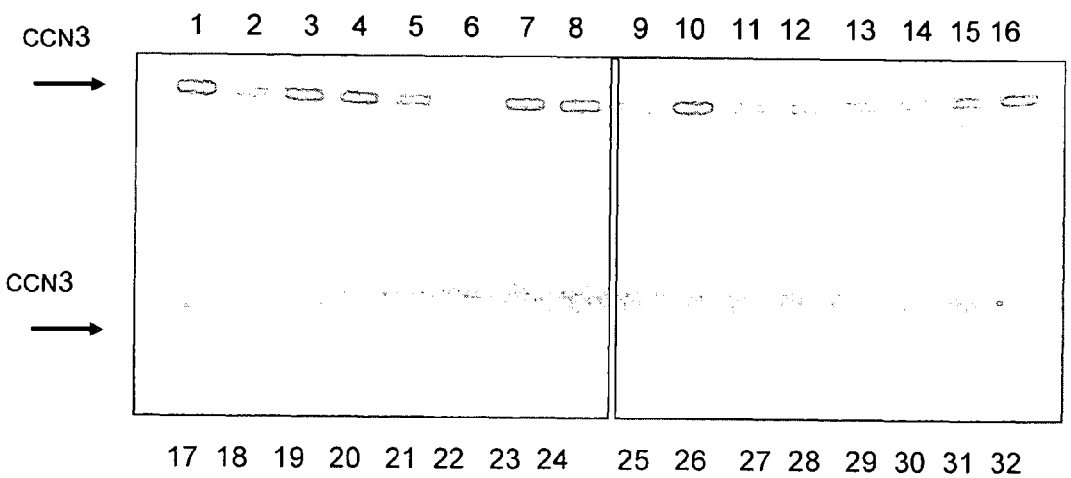
FIG. 6 is the result of reverse transcription-PCR using specific primer sequences, demonstrating low CCN3 mRNA levels in the kidney (primarily renal cortex) of healthy control non-diabetic mice (db/m, 17-32, upper figure, lower bands) at approximately 8 months of age. Expression of CCN3 was markedly increased after 7 months of diabetes and 8 months of age (db/db, 1-16, upper panel, upper bands), when animals are in a "static, disease condition" and progression has stabilized. The amount of the corresponding beta actin (housekeeping gene) levels were similar in both groups of animals (lower panel)
Figure 6:
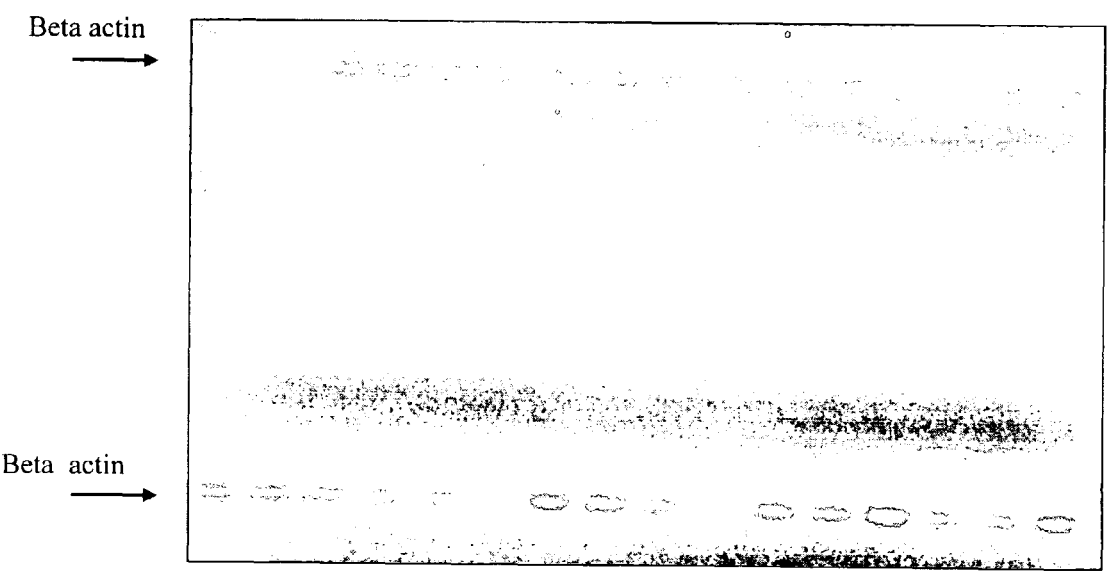
Figure 7:
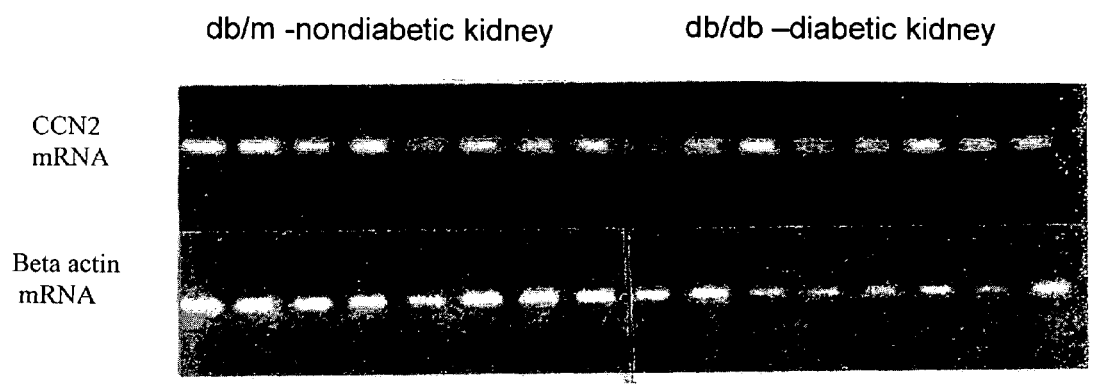
FIG. 7 is the result of reverse transcription-PCR using CCN2 specific primer sequences, demonstrating the corresponding CCN2 mRNA levels in the kidney (primarily renal cortex) of healthy control non-diabetic db/m mice m) at approximately 8 months (top left quadrant of figure). Expression of CCN2 was returned to normal after 7 months of diabetes in the db/db mice, when animals were in a "static" condition with no further progression of disease (top right quadrant). The expression of corresponding beta actin levels is shown in bottom lane half of the figure, a housekeeping gene). Each band in a figure represents results from an individual animal.

Reverse transcription-PCR for CCN3 mRNA (FIG. 6) demonstrated that mRNA levels of CCN3 were dramatically upregulated in the kidney at 6 months of disease (the only period examined). Renal CCN2 mRNA is greatly upregulated early (at 4-5 months as shown in previous studies (Riser B. L., et al, Urinary connective tissue growth factor (CTGF): a possible predictor of diabetic nephropathy (DN): *J Am Soc Nephrol,* 11:121A, 2000). By the 6 month period used in the current study CCN2 is only slightly elevated (see FIG. 7). This supports the idea that when CCN3 is expressed in high amounts, it may act to reduce the expression and/or activity of CCN2. This may explain the "static" disease condition in these animals that do not progress further. The increased CCN3 mRNA in the kidney tissue also provides evidence that the kidney cells are at least one source of the CCN3 observed in urine. In addition, we have also discovered, using immunostaining for CCN3, that CCN3 protein was also present in mouse-kidney sections of these diabetic mice.

Data from an in vitro Model of Renal Disease and Fibrosis

Renal mesangial cells play a key role in many renal diseases, including CKD, and that involving diabetes. This cell both produces and responds to many cytokines and growth factors and is important in mediating the common lesion of mesangial fibrosis/sclerosis. As is the case in vivo, kidney mesangial cells in culture respond to TGF-β (a well-established pro-fibrotic/sclerotic cytokine) by increasing CCN2, and in turn collagen (an extracellular matrix molecule important in fibrosis). This provides an in vitro model for fibrosis occurring in the kidney (and other organs as well). In this model, CCN2 is produced by these cells at low levels, but is significantly increased following exposure to TGF-β (2 ng/ml). TGF-β is a well-known stimulator or positive regulator of CCN2 in many other cells types as well.

Figure 8:
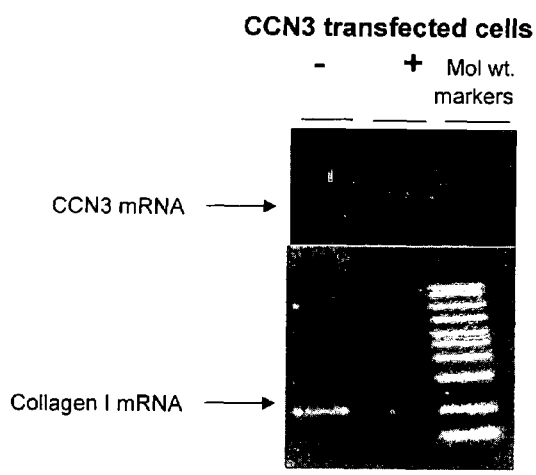
FIG. 8 shows the result of reverse transcription-PCR using CCN3 specific or collagen type I specific primer sequences, demonstrating that the specific overexpression of human CCN3 gene following in vitro transfection of mesangial cells resulted in a marked downregulation of collagen type I gene expression. Rat mesangial cells were transfected with either CCN3 gene construct (+), or a control Lac-Z gene construct (−)
Figure 9:
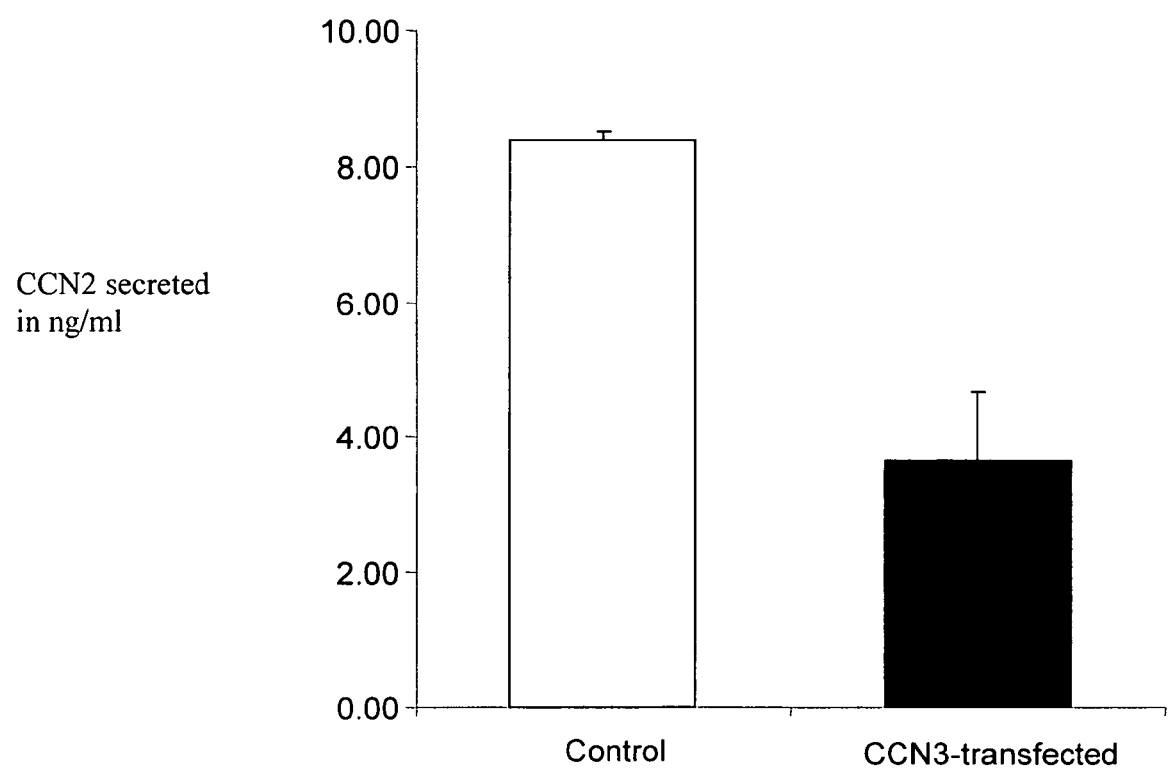
FIG. 9 shows the measurement by ELISA of CCN2 protein secretion in transfected mesangial cells, demonstrating that the transfection and subsequent overexpression of the CCN3 gene results in a marked reduction in the CCN2 secreted.
Figure 10:
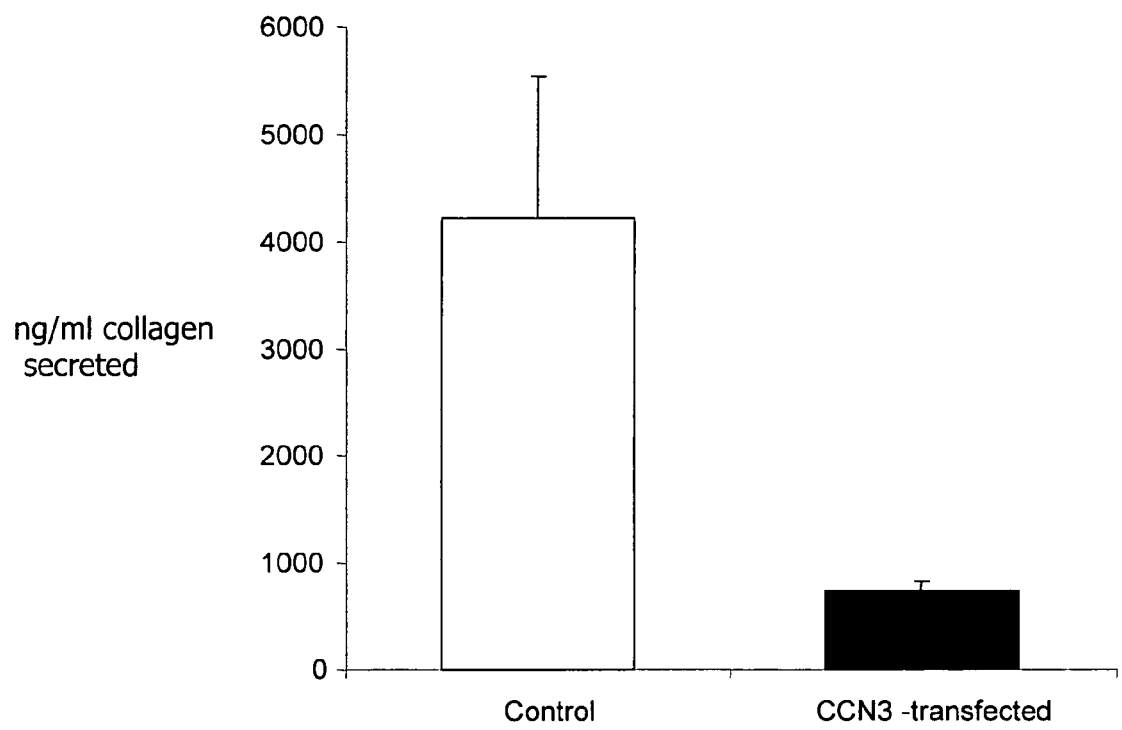
FIG. 10 shows the measurement by enzyme-linked immunosorbant assay (ELISA) of collagen type I protein secretion in transfected mesangial cells, and demonstrated that the specific overexpression the CCN3 gene in mesangial cells results in a blockade of collagen produced and/or accumulated.
Figure 11:
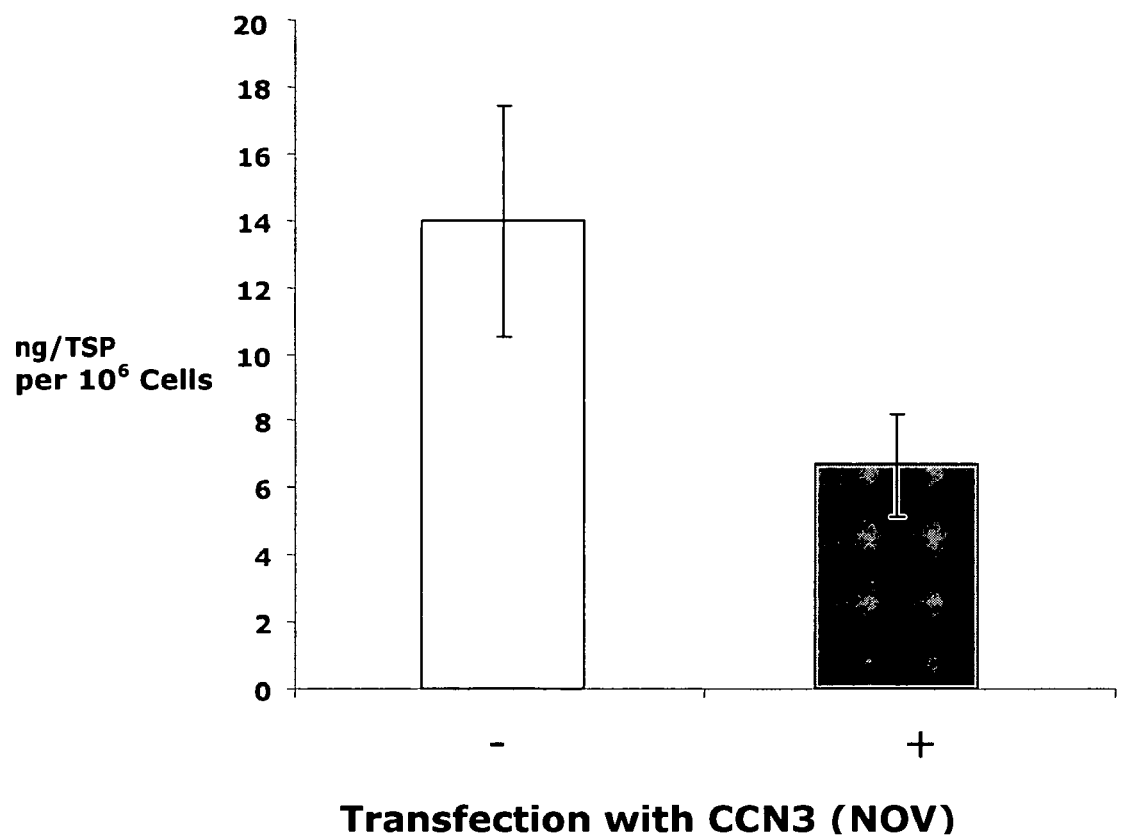
FIG. 11 shows the measurement by enzyme-linked immunosorbant assay (ELISA) of thrombospondin 1 (TSP-1) protein secretion in mesangial cells, and demonstrated that the specific overexpression the CCN3 gene resulted in the substantial reduction in TSP-1 secretion.

We examined whether mesangial cells were capable of producing CCN3 and if so the response to TGF-β. In our experiments, cultured mesangial cells were found to secrete relatively high levels, approximately 6.7 ng CCN3/100,000 cells). When the cells were exposed to TGF-β (2 ng/ml), the CCN3 level was reduced significantly to 2.2 ng, i.e. a near 70% reduction, while at the same time CCN2, and collagen accumulation was increased by a similar amount. This supports the idea of inverse (or negative) regulation of CCN2 and CCN3, and inverse roles in fibrosis/sclerosis. When CCN3 levels decrease, CCN2 levels (activity) increase, and ECM accumulates. To determine if elevated CCN3 levels then act to reduce CCN2 production or activity and result in a reversal or prevention of sclerosis/fibrosis, two sets of experiments were conducted. First, mesangial cells were treated with TGF-β in the presence or absence of conditioned culture medium enriched for CCN3. TGF-β enhanced CCN2 and collagen type I accumulation in mesangial cells is a well accepted in vitro model for fibrosis development and progression. This conditioned medium was from a human tumor cell line named NCI. These cells have been shown to secrete marked levels of CCN3. The results demonstrated that the enhanced productions of CCN2 and collagen (normally stimulated by TGF-β) were both markedly inhibited in the presence of NCI conditioned medium. Since this conditioned medium contains, in addition to CCN3, other proteins released for the cells, a second set of experiments was conducted to verify a CCN3-specific effect. To accomplish this, we cloned and transfected the gene for CCN3 into mesangial cells, with the control cells receiving the lac Z gene. The resulting cell lines showed a marked elevation of constituative expression of CCN3 mRNA (CCN3+ line) in those receiving the CCN3 gene, whereas those receiving the lac-z.gene (CCN3-line) remained unchanged (FIG. 8). As hypothesized, this specific upregulation in expression of CCN3 mRNA was shown to result in concomitant and substantial reduction in collagen type I mRNA levels (FIG. 8). Protein analysis showed that this upregulation in CCN3 gene expression resulted in a substantial reduction CCN2 secreted (FIG. 9), and a near total (97%) inhibition in collagen type I resulted (FIG. 10). A second extracellular matrix protein and a profibrotic factor, TSP-1, was also greatly reduced as a result of the increased expression of CCN3 (FIG. 11). Although it has been reported that CCN2 plays a role in the upregualtion of TSP-1 (Wang S. Denichilo M. Brubaker C. Hirschberg R. Connective tissue growth factor in tubulointerstitial injury of diabetic nephropathy. *Kidney International.* 60(1):96-105, 2001) and down-regulating CCN2 by CCN3 is likely a mechanism for CCN3 to reduce the formation of TSP-1 in this study, the present data does not rule out that CCN3 plays a direct role in inhibiting the secretion of TSP-1

Urine and/or Peritoneal Washings (Dialysis Fluids) from Peritoneal dialysis patients as a Source of Biologically Active CCN3 (nov) Protein CCN3 Proteins in the Peritoneal Dialysis (PD) Fluid and Serum of Patients We found that most peritoneal dialysis patients had levels of CCN3 (NOV) proteins in the PD fluids in the 20 ng/ml or higher range. In contrast, most patients did not have detectable levels of CCN2 (CTGF) proteins in the PD fluid. Only a few patients had measureable CCN2 values. Serum from healthy subjects showed approximately 700 ng/ml CCN3 using indirect ELISA with CCN3 (NOV) specific antibody used for this measurement. Western blotting confirmed that (in a large number of PD patients) PD fluids contained CCN3 protein and that CCN3 amount and molecular form varies among patients (FIG. 4). These data also provide evidence that PD fluids, along with urine discussed earlier, is an excellent source to isolate and purify CCN3 protein, or its fragments thereof, or its isoforms, or any combinations thereof. It is contemplated that CCN3 protein, active fragments, isoforms, or combinations thereof, can also be isolated and purified from other body fluids (e.g., blood) and tissues (e.g., kidney cells).

These molecules can be isolated and purified from the sources mentioned earlier by any standard bioseparation techniques, or a combination of bioseparation steps, which are well known to those skilled in the art. Example of well known bioseparation techniques include but are not limited to dialysis, molecular size exclusion chromatography, immunoisolation, affinity chromatography, gel electrophoresis (one-dimensional or two-dimensional), isoelectrofocusing, high performance liquid chromatography, pH gradient chromatography, ionic strength gradient chromatography, counter current chromatography, ion chromatography, etc.

The isolated and purified CCN3 protein or its fragments or isoforms (or combinations) of CCN3 can be potentially used in the treatment of diseases associated with aberrant levels of CCN2 by regulating the expression and/or activity of the CCN2 protein. The level of CCN3 in tissue or body fluids can also be used to predict, diagnose and/or follow the progression of diseases as well as to determine the effectiveness of therapeutic intervention.

The present invention, therefore, discloses a method for regulating CCN2 activity level in a subject by regulating CCN3 gene expression or CCN3 activity level of the subject. The subject can be of any species such as mammalian (e.g., human, rodents etc.) or avian subjects. In a preferred embodiment, the subject is human. What is meant by "CCN3" is any molecular species related to the CCN3 protein, including the full length CCN3 protein, a fragment thereof, an isoform, a complex comprising any form of CCN3, a recombinant CCN3 protein molecule, a mimetic to the CCN3 molecule, or a combination thereof. The term "isoform: in the present application means a protein molecule that has immunoreactivity with an antibody specific to CCN3. The antibody can be monoclonal or polyclonal. In an embodiment, the CCN3 activity is measured by the immunoreactivity to one or more antibodies against the full length CCN3 protein molecule (and in some cases a monoclonal antibody specific for short sequences and/or epitopes unique to CCN3) using standard immunoassay techniques such as ELISA or western blot.

In an embodiment, the regulation of the CCN2 (CTGF) gene expression is by downregulation and wherein the CCN2 gene expression is downregulated by enhancing the CCN3 (NOV) gene expression or by increasing the level of the CCN3 activity in the subject. In a preferred embodiment, the level of CCN3 activity in the subject can be increased by administering an effective amount of CCN3, which can be the full length CCN3 molecule, a fragment thereof, an isoform of CCN3, a complex comprising any form of CCN3, a recombinant CCN3, or a molecular mimetic of the CCN3 protein. An example of an effective amount of CCN3 is an amount to provide a serum full length CCN3 level of about 900 ng/ml or greater. Another example of an effective amount of CCN3 is administering one or more doses of CCN3 to the subject to provide a urinary CCN3 level of about 280 μg/mmol creatine or greater. It is contemplated that regulation of CCN2 by CCN3 can be used to treat any diseases associated with aberrant levels of CCN2 discussed earlier, which include but are not limited to chronic kidney disease, fibrosis or sclerosis, and cancer.

One of the potential uses of the method in the present invention is for the treatment of fibrosis. The term "fibrosis" used in the present disclosure includes fibrosis and/or sclerosis since they are similar processes and both have been shown to have CCN2 as at least one causal factor. In the present disclosure, "fibrosis" and "sclerosis" can be used interchangeably. The fibrosis can be associated with any organ capable of forming fibrosis, such as (but are not limited to) kidney, heart, liver, lungs, vasculature (including scleroderma, coronary arteries), cervix, eye, gums, brain, and the peritoneum. The fibrosis can also be the result of one of the pathological conditions such as (but are not limited to) renal diseases, peritoneal dialysis, macular degeneration, periodontal disease, congestive heart failure, stroke and related ischemia and reperfusion injury, surgical and medical intervention procedures (e.g., balloon angioplasty, insertion of stents, catheters, grafts (including arterial and venous fistulas), and organ transplants), and unwanted post-surgical tissue or organ adhesions. The fibrosis can also be associated with increased cellular proliferation, for example, glomerular proliferative disease. Other indications are associated with abnormal cellular proliferation, for example, cancer, particularly when growth or metastasis is related to upregulation of CCN2 expression.

The present invention is also related to a method for treating renal fibrosis in chronic kidney disease in a subject by administering an effective amount of CCN3 to the subject, wherein the CCN3 is selected from the group consisting of: a full length CCN3 protein, a fragment thereof, an isoform of the full length CCN3 protein; a molecular mimetic of CCN3, a recombinant CCN3 protein, a complex comprising CCN3, and a combination thereof. An example of an effective amount of CCN3 is administering one or more doses of full length CCN3 to the subject to provide a serum level of 900 ng/ml or greater. Another example of an effective dose of the full length CCN3 is an amount sufficient to provide an urinary CCN3 level of about 280 μg/mmol creatine or greater. For patients undergoing peritoneal dialysis with a dialysis fluid, the CCN3 can be administered to the subject by adding the CCN3 to the dialysis solution to be used by the patient undergoing peritoneal dialysis. In this embodiment, an example of an effective amount of the full length CCN3 is a concentration of the full length CCN3 protein of 100 ng/ml of dialysis solution or greater, such as 500 ng/ml or greater, or 1000 ng/ml or greater.

The present invention further relates to a kit for treating fibrosis or sclerosis, or any other diseases related to an aberrant level of CCN2. The kit comprises CCN3 selected from the group consisting of: a full length CCN3 protein, a fragment thereof, an isoform of the full length CCN3 protein; a molecular mimetic of CCN3, a recombinant CCN3 protein, a complex comprising CCN3, and a combination thereof.

The present invention can also be used for diagnosing diseases, such as renal disease or fibrotic/sclerotic disorder in a subject. The method comprises: (a) obtaining a tissue or body fluid sample from the subject, (b) detecting the level of CCN3 activity in the sample, and (c) comparing the level of CCN3 activity in the sample to a standard level, wherein an increased level of CCN3 activity is indicative of the presence of the disease. In an embodiment, the presence or absence of a unique isoform of CCN3 can be used to be indicative of a disease. The sample can be a tissue or a body fluid, such as the urine, blood (including plasma and serum), or peritoneal wash. In a preferred embodiment, the level of CCN3 activity is detected by an immunoassay.

The present invention further relates to a diagnostic kit for use in diagnosing renal or fibrotic disorder in a mammalian subject. The kit comprises an antibody specific to CCN3. The antibody can be monoclonal or polyclonal antibody The practice of the present invention will employ and incorporate, unless otherwise indicated, conventional techniques of cell biology, cell culture, molecular biology, microbiology, genetic engineering, and immunology, which are within the skill of the art. While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims. The appended claims should be construed broadly and in a manner consistent with the spirit and the scope of the invention herein.

I claim:

1. A method for reducing an accumulation of collagen associated with chronic kidney disease, renal fibrosis or renal sclerosis comprising:
   providing a human subject having an accumulation of collagen associated with chronic kidney disease, renal fibrosis or renal sclerosis;
   measuring a CCN3 level and/or a CCN2 level in the subject prior to the step of administering a full-length nephroblastoma overexpressed product or protein (CCN3) to the subject;
   administering to the human subject a full-length nephroblastoma overexpressed gene product or protein (CCN3) to reduce accumulation of collagen in the subject; and
   measuring the CCN3 level and/or a CCN2 level in the subject after the step of administering and confirming the CCN3 level is higher in the subject than before the administering step or confirming the CCN2 level is lower in the subject than before the administering step to verify a reduction in the accumulation of collagen in the subject.

2. The method of claim 1, wherein the level of CCN3 and/or CCN2 is detected in a tissue or body fluid sample from the subject.

3. The method of claim 2, wherein the body fluid sample is urine, blood, serum, plasma, or peritoneal wash.

4. The method of claim 1, wherein the level of CCN3 and/or CCN2 is detected by an immunoassay.

5. The method of claim 1, wherein the renal fibrosis or sclerosis is associated with increased cellular proliferation.

6. The method of claim 5, wherein the cellular proliferation results in glomerular proliferative disease.

7. The method of claim 1, wherein the subject undergoes peritoneal dialysis with a dialysis solution having the CCN3 protein.

8. The method of claim 1, wherein the CCN3 protein is administered to the subject by intramuscular, intravenous, oral, nasal, topical or transdermal administration, or by inhalation.

9. A method for reducing an accumulation of collagen associated with chronic kidney disease, renal fibrosis or renal sclerosis comprising:
   providing a human subject having an accumulation of collagen associated with chronic kidney disease, renal fibrosis or renal sclerosis; and
   administering at least one dose of full-length nephroblastoma overexpressed gene product or protein (CCN3) to the subject to provide a serum level of about 900 ng/mL or greater to the subject to reduce the accumulation of collagen in the subject associated with chronic kidney disease, renal fibrosis or renal sclerosis.

10. A method for reducing an accumulation of collagen associated with chronic kidney disease, renal fibrosis or renal sclerosis comprising:
   providing a human subject having an accumulation of collagen associated with chronic kidney disease, renal fibrosis or renal sclerosis; and
   administering at least one dose of full-length nephroblastoma overexpressed gene product or protein (CCN3) to the subject to provide a urinary level of about 280 µg/mmol creatine or greater to the subject to reduce the accumulation of collagen in the subject associated with chronic kidney disease, renal fibrosis or renal sclerosis.

* * * * *